(12) United States Patent
Glocker et al.

(10) Patent No.: US 10,195,111 B2
(45) Date of Patent: Feb. 5, 2019

(54) CONTAINER, HOLDING DEVICE, HOLDING SYSTEM AND INJECTION AID

(75) Inventors: Joachim Glocker, Weingarten (DE); Tilman Roedle, Wolfegg (DE)

(73) Assignee: VETTER PHARMA-FERTIGUNG GMBH & CO., KG., Ravensburg (DE)

( * ) Notice: Subject to any disclaimer, the term of this patent is extended or adjusted under 35 U.S.C. 154(b) by 0 days.

(21) Appl. No.: 14/003,191

(22) PCT Filed: Mar. 21, 2012

(86) PCT No.: PCT/EP2012/001304
§ 371 (c)(1),
(2), (4) Date: Sep. 4, 2013

(87) PCT Pub. No.: WO2012/126636
PCT Pub. Date: Sep. 27, 2012

(65) Prior Publication Data
US 2014/0158700 A1 Jun. 12, 2014

(30) Foreign Application Priority Data

Mar. 21, 2011 (DE) .......................... 10 2011 015 112

(51) Int. Cl.
*A61J 1/16* (2006.01)
*A61M 5/00* (2006.01)
(Continued)

(52) U.S. Cl.
CPC ................. *A61J 1/16* (2013.01); *A61J 1/062* (2013.01); *A61M 5/002* (2013.01); *A61M 5/008* (2013.01);
(Continued)

(58) Field of Classification Search
CPC ............ A61J 1/16; A61J 1/062; A61M 5/002; A61M 5/008; A61M 5/284; A61M 5/3137; A61M 5/344
(Continued)

(56) References Cited

U.S. PATENT DOCUMENTS 2,833,007 A 5/1958 Messer, Sr. et al.
4,782,957 A 11/1988 Kernodle, Sr.
(Continued)

FOREIGN PATENT DOCUMENTS

DE 202008014334 U1 2/2009
EP 2119463 A1 11/2009
(Continued)

OTHER PUBLICATIONS

International Preliminary Report on Patentability regarding International Application No. PCT/EP2012/001304 dated Sep. 24, 2013.
(Continued)

*Primary Examiner* — James N Smalley
*Assistant Examiner* — Madison L Poos
(74) *Attorney, Agent, or Firm* — Stephen T. Olson; Harness, Dickey & Pierce, P.L.C.

(57) ABSTRACT

A container for pharmaceutical preparations includes a base body. The container has at least one first holding element embodied such that it can work together with a corresponding second holding element of a holding device for the container in order to hold the base body securely on the holding device.

20 Claims, 14 Drawing Sheets

(51) Int. Cl.
*A61J 1/06* (2006.01)
*A61M 5/28* (2006.01)
*A61M 5/31* (2006.01)
*A61M 5/34* (2006.01)

(52) U.S. Cl.
CPC .......... *A61M 5/284* (2013.01); *A61M 5/3137* (2013.01); *A61M 5/344* (2013.01)

(58) Field of Classification Search
USPC ........ 220/737, 23.88, 23.89; 206/534.1, 366, 206/370, 558, 560, 562–565; 422/300; 53/425
See application file for complete search history.

(56) References Cited

U.S. PATENT DOCUMENTS

| | | | |
|---|---|---|---|
| 4,801,012 A * | 1/1989 | Steenhuisen et al. | 206/366 |
| 5,338,309 A * | 8/1994 | Imbert | 604/187 |
| 5,921,966 A | 7/1999 | Bendek et al. | |
| 6,164,044 A * | 12/2000 | Porfano et al. | 53/471 |
| 6,290,680 B1 | 9/2001 | Forsberg et al. | |
| 6,569,127 B1 * | 5/2003 | Fago et al. | 604/218 |
| 6,722,054 B2 * | 4/2004 | Yarborough et al. | 34/284 |
| 6,807,797 B2 | 10/2004 | Forsberg et al. | |
| 7,100,768 B2 * | 9/2006 | Grimard et al. | 206/438 |
| 7,264,612 B2 * | 9/2007 | Nemoto | 604/154 |
| 7,296,678 B2 | 11/2007 | Raynal-Olive et al. | |
| 2003/0028102 A1 * | 2/2003 | Nemoto | 600/432 |
| 2005/0224382 A1 * | 10/2005 | Raynal-Olive et al. | 206/438 |
| 2006/0249520 A1 * | 11/2006 | DeMonte | 220/737 |
| 2007/0151882 A1 * | 7/2007 | Cocheteux | A61M 5/008 206/366 |
| 2009/0254043 A1 | 10/2009 | Van Bulow et al. | |
| 2010/0012546 A1 | 1/2010 | Togashi et al. | |
| 2010/0089925 A1 * | 4/2010 | Peltier | B01L 3/5082 220/288 |
| 2011/0005958 A1 * | 1/2011 | Stepovich et al. | 206/524.1 |
| 2012/0118777 A1 * | 5/2012 | Kakiuchi et al. | 206/366 |

FOREIGN PATENT DOCUMENTS

| | | |
|---|---|---|
| JP | 11104240 A | 4/1999 |
| WO | WO-99/015215 A1 | 4/1999 |
| WO | WO-03/094999 A1 | 11/2003 |
| WO | WO-2004/091700 A1 | 10/2004 |
| WO | WO-2011/0015896 A1 | 2/2011 |

OTHER PUBLICATIONS

International Search Report (English and German) and Written Opinion of the ISA (German) for PCT/EP2012/001304, ISA/EP, Rijswijk, NL, dated Jul. 9, 2012.
Office Action issued in parallel procedure in Russia, No. 2412-198458RU/3204, dated Oct. 8, 2016. Machine translation provided.
Japanese Office Action in the parallel application JP 2014-500287, JPO, dated Sep. 26, 2017, with English translation thereof.
Japanese Office Action for related application JP 2018-008492, JPO, dated Oct. 2, 2018, with English translation attached.

* cited by examiner

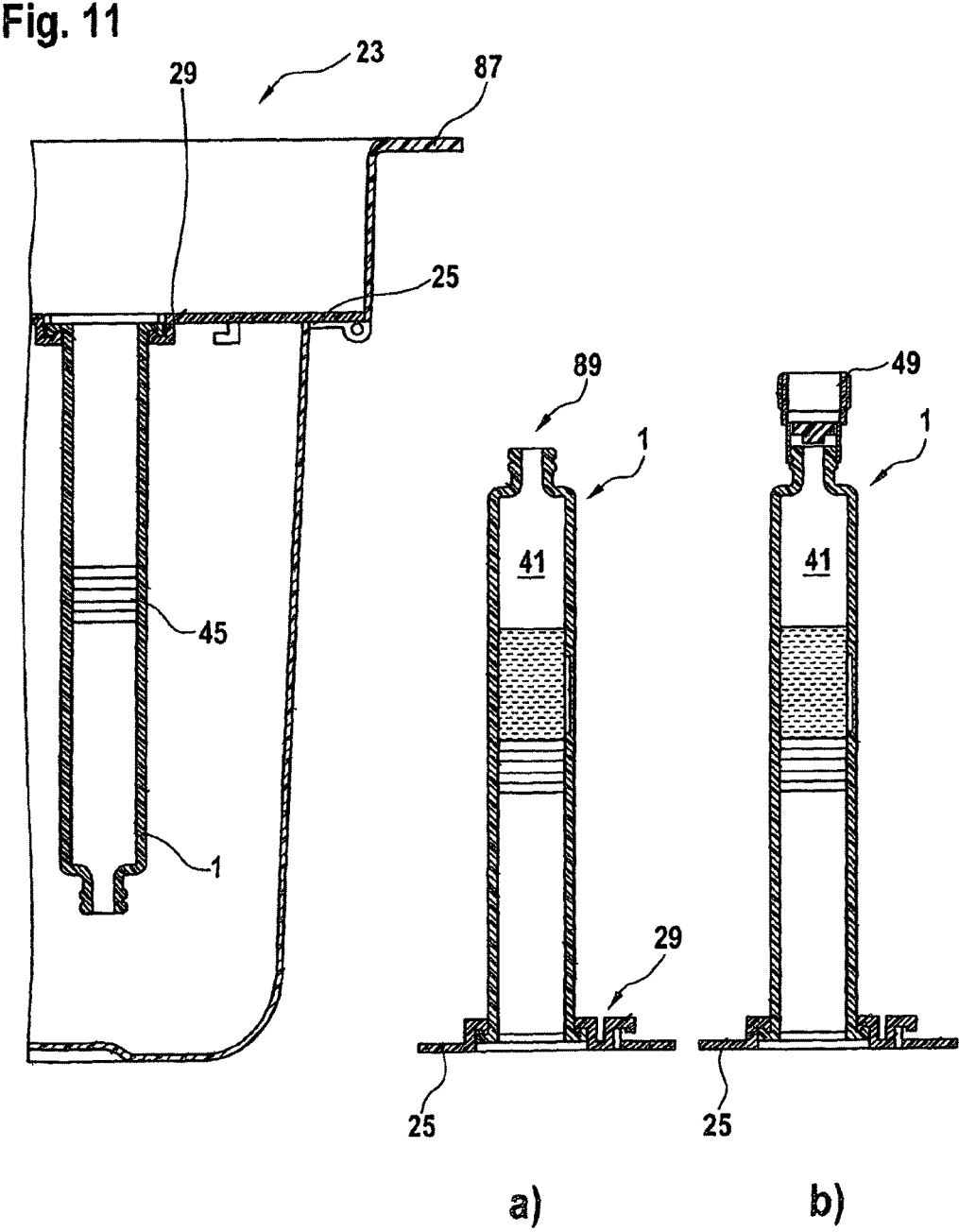

CONTAINER, HOLDING DEVICE, HOLDING SYSTEM AND INJECTION AID

CROSS-REFERENCE TO RELATED APPLICATIONS

This application is a 371 U.S. National Stage of International Application No. PCT/EP2012/001304, filed Mar. 21, 2012, which claims priority to German Patent Application No. DE 10 2011 015 112.5, filed Mar. 21, 2011. The entire disclosures of each of the above applications are incorporated by reference herein.

FIELD

The invention relates to a container for pharmaceutical preparations, a holding device for containers, a holding system for containers and an injection aid.

BACKGROUND

Containers for pharmaceutical preparations, holding devices and holding systems for such containers as well as injection aids are known. The holding devices can, for example, be embodied as carrier systems for a holding system for pharmaceutical containers or be comprised by an injection aid. The containers have a base body and are preferably embodied as a syringe, carpule, vial, or preferably also as a dual-chamber system. Typically, such containers of the pharmaceutical industry for filling with pharmaceutical preparations such as, for example, medications, are delivered already washed and/or sterilized. For this purpose, several containers are preferably combined in a holding system. They are arranged more or less loosely in a carrier system, so relative movement between the containers and the carrier system on the one hand and the individual containers on the other hand are possible. This can lead to cosmetic defects in the containers. If they are embodied as dual chamber systems, they must be turned in order to fill both chambers. Due to the loose arrangement in the carrier system, the containers must be removed for this purpose from same and sorted into storerooms provided specifically for this purpose. This means an additional work step; it is also possible for cosmetic defects to be caused to the containers when they are handled for resorting. Containers that are embodied as carpules are often used in conjunction with injection aids, for example so-called auto-injectors or pens. The injection aid comprises a front housing part for receiving the carpule and a mechanical part which comprises an activation and triggering mechanism. A carpule cannot be connected to the mechanical part without the front housing part. Overall, it is therefore a drawback in known containers that they cannot be connected in an appropriate manner, for example with a carrier system or with a mechanical part, to an injection aid, generally to a holding device, so that they are held securely and firmly on same.

SUMMARY

It is therefore the object of the invention to provide a container and a holding device which do not have the abovementioned drawbacks.

The object is achieved by a container for pharmaceutical preparations with the features of claim 1. It is characterized by at least one holding means which is embodied such that it can work together with a corresponding holding means of a holding device for the container in order to hold the base body securely on the holding device. The holding means is provided with respect to the base body such that holding forces can be introduced into the base body, with the result that the container is ultimately held securely on the holding device. As a result, it is possible to connect it for example to a carrier system of a holding system such that no undesired relative movements can occur between the container and the carrier system on the one hand and different containers arranged in the carrier system on the other hand. Furthermore, the container can be handled together with the carrier system. If several containers are arranged on the carrier system, only the carrier system need be grasped, transported and turned—the latter particularly in connection with the filling of dual chamber systems—without the need to separate individual containers out of the carrier system. By virtue of the holding means, such a container, for example one that is embodied as a carpule, can also be connected to the mechanical part of an injection aid without the need for a front housing part for receiving the container.

A container is preferred in which the holding means comprises at least one projection and/or at least one recess. The projection and/or the recess is/are preferably provided on a circumferential surface of the base body. The projection and/or the recess can work together with at least one corresponding projection and/or at least one corresponding recess in such a way that a positive connection of the container to the holding device is preferably created.

A container is preferred, for example, in which the holding means is embodied such that they can work together with a corresponding holding means in the manner of a bayonet joint. The holding means can therefore comprise, for example, grooves that are substantially perpendicular to each other and into which the appropriately embodied projections of the corresponding holding means engage in order to form a connection in the manner of a kind of a plug-and-turn mechanism such as that typically encountered in a bayonet joint. As will readily be understood, it is also possible for the holding means of the container to have corresponding projections which engage in grooves of the corresponding holding means that are substantially perpendicular to each other.

A container is also preferred in which the holding means is provided on a proximal end of the base body. If the container is embodied as a syringe, carpule or dual chamber system, it has a proximal and a distal end. The proximal end is especially suited here for providing holding means. Especially preferably, the holding means is provided at a distance from the proximal end of the base body.

A container is also preferred that has a connecting element. This is embodied such that it can receive a tool in a positive-fitting manner. The tool is used to effect a relative rotation between a holding device and the container in order to lock or unlock it at the holding device. For this purpose, the connecting element is embodied such that torque transmission from the tool to the base body of the container is possible, thus enabling a connection between the holding means and a corresponding holding means.

Finally, a container is preferred that is embodied as a syringe, carpule, vial or, preferably, as a dual chamber system.

Further preferred sample embodiments follow from the subclaims.

The object is also achieved through the provision of a holding device with at least one receptacle for a container and is characterized in that the receptacle comprises at least one holding means which is embodied such that it can work together with at least one corresponding holding means of a container for pharmaceutical preparations such that a base body of the container is held securely on the holding device. Retaining forces can therefore be transferred from the holding device into the base body so that it can be handled particularly together with the holding device.

A holding device is preferred in which the holding means is embodied such that unintentional relative movement between a container inserted into the receptacle and the holding device—when seen in the axial, radial and in the circumferential direction—is prevented. The container is therefore arranged securely and stably with respect to all possible degrees of freedom in the receptacle of the holding device. Unintentional relative movement cannot occur, so cosmetic defects can reliably be prevented. Nor can the container fall out of the holding device when it is turned.

A holding device is preferred in which the holding means is embodied such that it can work together with a corresponding holding means on a base body of a container. Therefore, if the holding means of the container comprises a projection, the holding means of the holding device preferably comprises a corresponding recess, and vice versa.

A holding device is preferred which is embodied as a carrier system for a holding system for pharmaceutical containers. Preferably, more than one receptacle is provided on the carrier system for more than one container. In this case, relative movement between the containers on the holding means provided on the receptacles is also reliably prevented. The ability to handle the carrier system with the containers as a unit results in a logistical advantage. It is not even necessary to grasp the individual containers. If dual chamber systems are inserted into the carrier system, it can be readily turned in order to fill the two chambers of the dual chamber systems because the dual chamber systems cannot fall out of the receptacles of the carrier system. Accordingly, separate hoppers no longer need to be used.

Finally, a holding device is preferred which is embodied as a mechanical part for an injection aid. In this case, since the mechanical part of the injection aid has a receptacle which comprises a holding means by means of which a container is securely held, the otherwise necessary front housing part of the injection aid can be omitted. Overall, an injection aid with the holding device can then comprise fewer parts, with the result that it can be manufactured more cost-effectively and with less logistical effort.

Further advantageous embodiments follow from the sub-claims.

It is also the object of the invention to provide a holding system which does not have the described drawbacks.

Further advantageous embodiments follow from the sub-claims.

Finally, it is also the object of the invention to provide an injection aid which does not have the cited drawbacks.

The holding device and the container can be connected to each other by the corresponding holding means, so a front housing part can be omitted. As a result, the injection aid can be manufactured with less material expense and in a logistically simpler manner, so the manufacture thereof is more cost-effective overall. Moreover, handling is simpler because, instead of three, only two elements have to be connected to each other.

DESCRIPTION OF THE DRAWINGS

In the following, the invention is explained in further detail on the basis of the figures.

DETAILED DESCRIPTION

Figure 1:
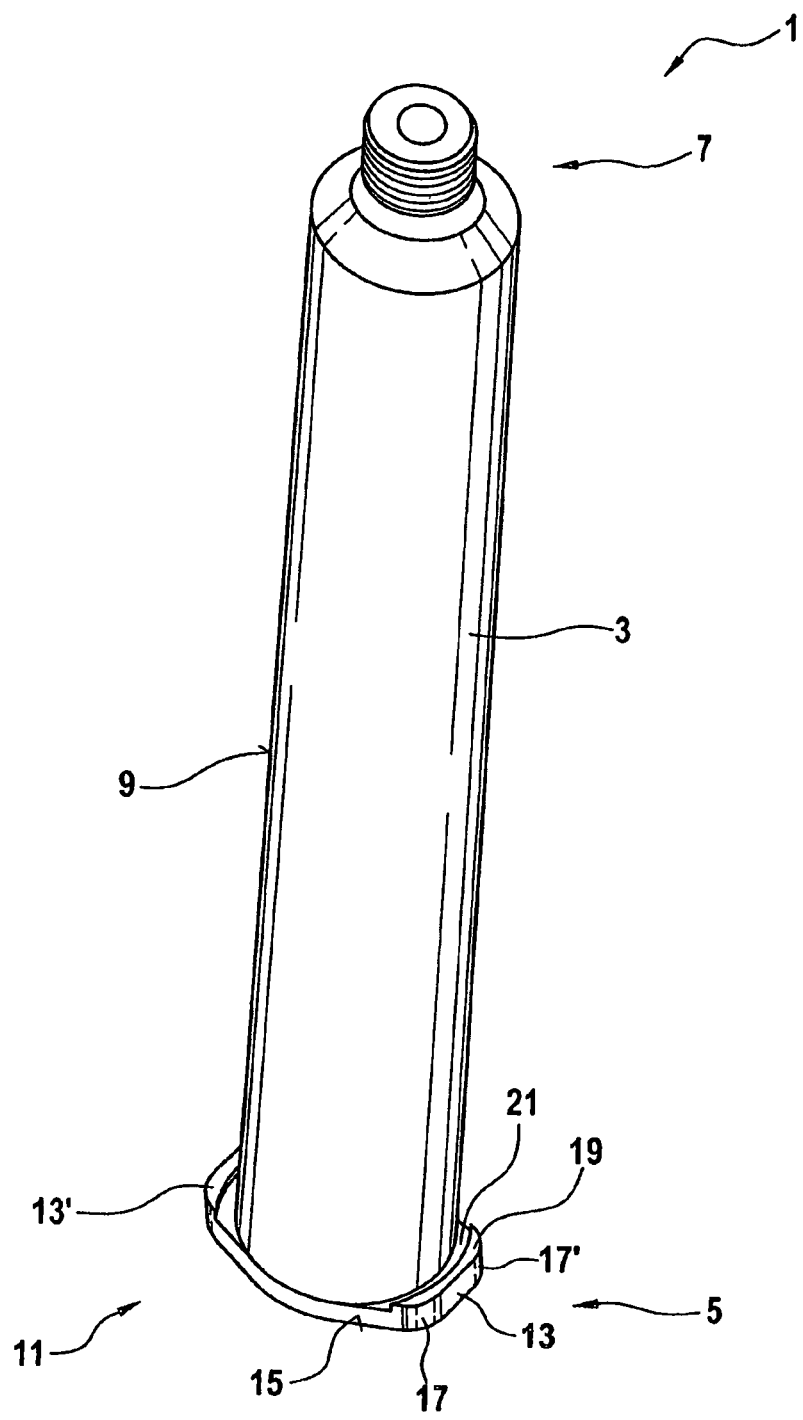
FIG. 1 shows a sample embodiment of a container for pharmaceutical preparations.

FIG. 1 shows a sample embodiment of a container 1 for pharmaceutical preparations. The container 1 is embodied here as a carpule, and it can be embodied as a single- or dual-chamber carpule. Preferably, the container is embodied as a dual-chamber carpule. In other sample embodiments (not shown), the container is preferably embodied as a syringe, particularly a single- or dual-chamber syringe, or as a vial.

The container 1 has a base body 3 which is preferably cylindrical.

If the container 1 is embodied as a syringe or—as shown here—as a carpule, it comprises a proximal end 5 and a distal end 7. The base body 3 has a circumferential surface 9.

At least one holding means 11 is preferably provided on the base body 3. This [holding means] is embodied such that it can work together with a corresponding holding means of a holding device for the container in order to securely hold the base body on the holding device. This means that retaining forces can be transferred via the holding means 11 into the base body 3 in order to hold it. For this, it is not necessary for the holding means 11 to be arranged directly on the base body or to be embodied in a single piece therewith. What is essential is that it be provided such that the retaining forces can be transferred into the base body 3.

However, in the preferred sample embodiment shown, the holding means 11 is provided directly on the base body 3. It is preferably embodied in a single piece therewith.

The base body 3 can preferably comprise glass or plastic. Cosmetic defects must be feared particularly if the base body 3 comprises plastic. The holding means 11 is preferably molded directly on the base body 3 if the latter comprises glass or plastic.

The holding means 11 preferably comprises at least one projection and/or at least one recess. In this way, it is possible for corresponding projections and/or recesses of the holding means of the container 1 on the one hand and of a holding device for same on the other hand to engage in each other, preferably in a positive-fitting manner, in order to hold the container 1 on the holding device. Preferably, the projection or the recess is provided on the circumferential surface 9.

Preferably, the holding means 11 comprises at least two projections and/or recesses which are preferably provided on a circumferential line of the circumferential surface 9 and especially preferably at the same angular distance from each other.

It is possible for the container 1 to comprise at least one axial projection and/or at least one axial recess.

Here, the axial direction corresponds to the direction of the longitudinal extension of the container 1. A radial direction is a direction that is perpendicular to a longitudinal axis of the container 1. A circumferential direction is a direction that extends around the longitudinal axis of the container 1.

In another preferred sample embodiment, the holding means 11 comprises at least one radial projection and/or at least one radial recess. These are also preferably arranged on the circumferential surface 9.

In the depicted sample embodiment, two opposing radial projections 13, 13'—when seen in a radial direction—are provided. In another sample embodiment (not shown), two radial recesses can be provided accordingly. It is also possible to provide both at least one radial projection and at least one radial recess, or to combine projections and recesses. In yet another sample embodiment, the angular division between the projections and/or recesses can be unequal. The elements then do not oppose each other.

In the depicted sample embodiment, the holding means 11 is provided on the proximal end 5 of the base body 3.

The projections 13, 13' are preferably identical. For this reason, only the projection 13 is discussed in the following, it being assumed that the projection 13' of the depicted sample embodiments is identical. Of course, it is also possible to provide different projections 13, 13'.

The projection 13 has on a circumferential surface 15 at least one radial neck, here two radial necks 17, 17'. In another sample embodiment, it is possible for the projection 13 to have at least one recess on its circumferential surface 15. In yet another sample embodiment, if the holding means 11 comprises a recess, it is possible for it to have at least one radial neck and/or at least one radial recess on its circumferential surface.

A radial neck 17, 17' or a corresponding radial recess is preferably provided in order to increase the friction of the holding means 11 on a corresponding surface of the holding means of a holding device. However, it is also possible for the neck 17, 17' or the corresponding recess to work together with a recess or a corresponding neck of the corresponding holding means such that a locking of the container 1 in the holding device practically results. In this respect, the der neck 17, 17' or a corresponding neck on the corresponding holding means can also be referred to as a locking element.

The projection 13 has at least one, here exactly one axial neck 19. As a result, a recess or groove 21 is formed—when seen in a radial direction—between the axial neck 19 and the circumferential surface 9. In another sample embodiment, instead of or in addition to the axial neck 19, at least one axial recess, preferably a groove can be provided on the projection 13. In yet another sample embodiment (not shown), if the holding means 11 comprises at least one recess, it is possible for it to have at least one axial neck and/or at least one axial recess, preferably a groove.

In the depicted sample embodiment, the projection 13—when seen in cross section, which is not shown—is more or less hook-shaped. This results from the fact that it comprises the axial neck 19 on the one hand and the axial recess 21 on the other hand. A corresponding holding means can engage behind the axial neck 19, thus resulting in a positive connection.

Preferably, the holding means 11 is embodied such that it can work together with a corresponding holding means in the manner of a bayonet joint. Typically, a bayonet joint comprises a plug-and-turn mechanism in which at least one projection on one part is first inserted in the longitudinal direction into a first recess provided on the other part, with a second, adjacent recess being substantially perpendicular to the first recess but—when seen in the direction of insertion of the projection—shifted forward. The projection must first travel a certain distance in a plugging motion along the first recess before it can subsequently be turned with the aid of a rotational motion into the second recess. Since the second recess extends substantially perpendicular to the first recess, the two parts then can no longer be separated by a merely translational relative movement. Usually, the bayonet joint—when seen in the longitudinal direction—is pretensioned, so that the projection is forced against the recess, thus resulting in a certain stiction.

The second recess can also run transversely to the first recess, in which case it then comprises a surface which—when seen counter to the direction of insertion—drops off. If the closure—when seen in the longitudinal direction—is pretensioned, a certain amount of force must first be applied in order to insert the projection into the second recess. The pretensioning force acting on the projection in the locking position is then less than this force. In order to unlock the two parts relative to each other, the appropriate greater force must again be applied. When in the locking position, the projection therefore is seated in a virtual minimum potential.

The term "locking position" refers hereinafter generally to the position of the container 1 on a holding device in which it is securely and firmly arranged on same. The term does not mean that there must necessarily be a catch mechanism between the corresponding holding elements.

The at least one projection and/or the at least one recess of the holding means 11 preferably has/have at least one declining surface. This can be embodied as the declining surface of a bayonet joint—as just described.

However, it is also possible for the at least one declining surface to be preferably provided as a lead-in chamfer for the fastening of the holding means on a corresponding holding means of a holding device. Such a lead-in chamfer can be used, for example, to displace an elastically mounted locking element upon insertion of the holding means 11, in which case the elastic locking element then engages in a catching manner into an undercut arranged in the area of the lead-in chamfer when the holding means 11 has been inserted far enough into the corresponding holding means. The container 1 is then securely locked on the holding device.

However, the lead-in chamfer can also preferably be provided in order to effect, upon connection of the corresponding holding means, a continuous compression or an increasing stiction. In particular, it is possible for there to be a self-locking between the corresponding holding means so that they are securely held together.

In general, it is possible for at least one projection and/or at least one recess of the holding means 11 to have at least one declining surface, with the at least one declining surface being provided as a lead-in chamfer for the fastening of the holding means on a corresponding holding means of a holding device.

Figure 2:
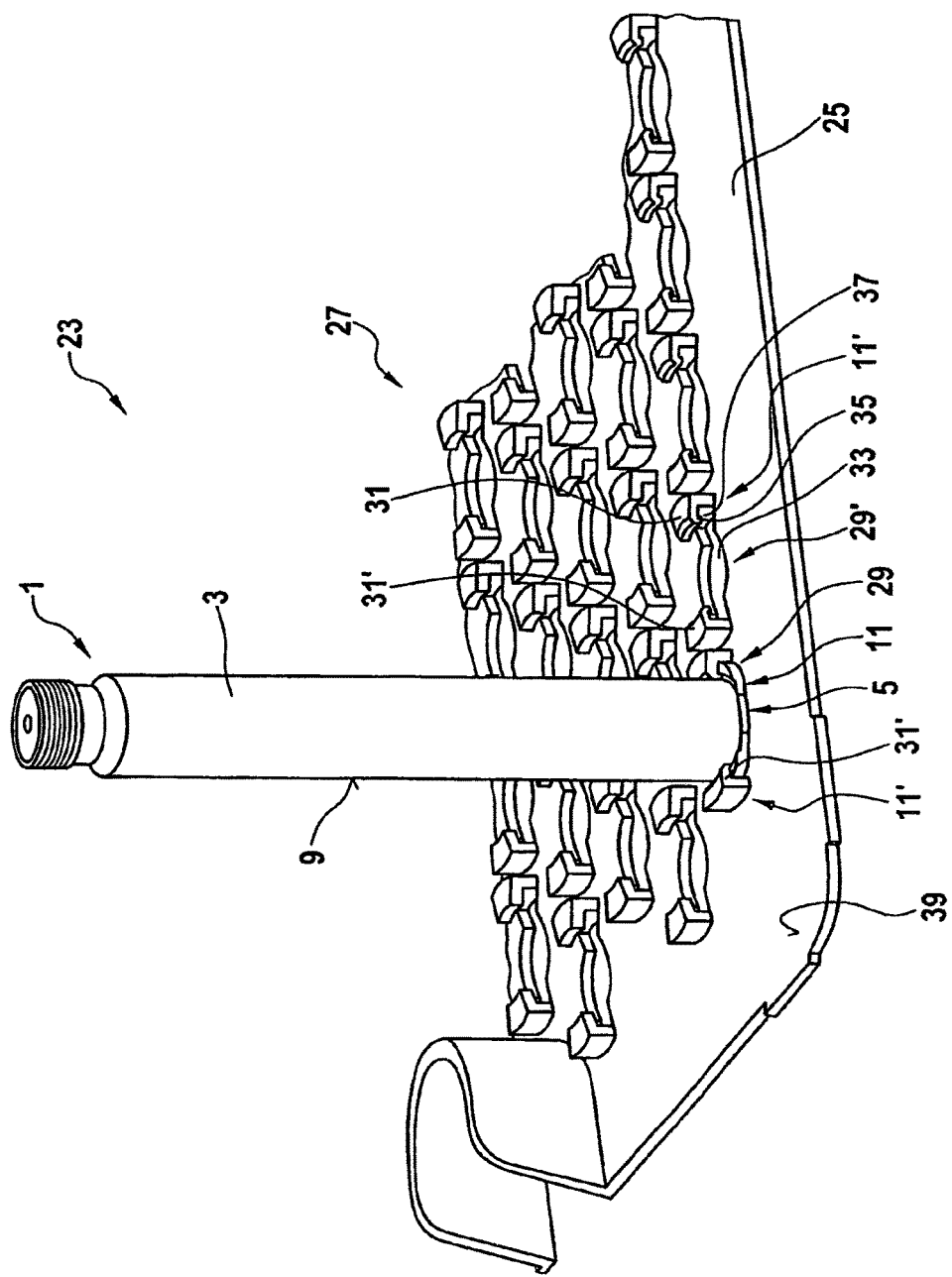
FIG. 2 shows a sample embodiment for a holding system and a holding device embodied as a carrier system.

FIG. 2 shows a sample embodiment of a holding system 23 for containers for pharmaceutical preparations with a holding device 27 embodied as a carrier system 25. The same and functionally equivalent elements are provided with the same reference symbols, so reference is made to the preceding description in that respect. A container 1 is arranged in a receptacle 29 of the holding device 27.

The carrier system 25 depicted here, which is embodied as a holding device 27, is preferably used in conjunction with a holding system 23 which further comprises a tub element (not shown) in which the carrier system 25 can be arranged. Such holding systems, which are used for transport, particularly the delivery and handling of a certain number of containers 1, are usually also referred to as a nest/tub configuration. The so-called tub is a tub element into which the carrier system 27 embodied as a nest can be inserted. Preferably, the tub is sealed by a film. In this way, it is particularly possible to transport and maintain sterile a certain number of containers 1 in a pre-sterilized state so that the containers 1 can be brought in the tub into a clean room for filling with the need for repeated sterilization thereof. With the aid of the nest and/or of the carrier systems 25, the containers 1 can be handled without having to be grasped individually.

Preferably, the dimensions of the carrier system 25 and of the tub element (not shown) are based on standardized packaging shapes. Consequently, the holding system 23 can be used in standardized fill lines. Known or existing mechanical and process technology can be applied, so no or only slight adaptations of existing system parts or known processes are necessary for the use of the holding system 23.

The holding device 25 shown in FIG. 2 comprises several receptacles 29 for containers 1 which are preferably identical. Consequently, reference is made in the following only to the receptacle 29 or to the receptacle 29' arranged adjacent to same. As will readily be understood, it is also possible to provide various receptacles on a holding device 27.

The receptacle 29, 29' comprises a holding means 11' which is embodied such that it works together with the corresponding holding means 11 of the container 1 such that the base body 3 is held securely on the holding device 27.

It is possible for the holding device 27 to comprise at least one receptacle having a diameter that is slight less than the outer diameter of the base body 3. If sufficient elasticity is provided either in the holding device 27 in the area of the receptacle 29 or in the base body 3, the two elements can then be connected through the insertion of the container 1 into the receptacle 29, upon which they hold together in a frictionally engaged manner. However, cosmetic defects can occur here, particularly in the area of the circumferential surface 9.

A sample embodiment of the holding device 27 is therefore preferred in which a positive fit is effected between corresponding holding means.

It is possible here for the holding device 27 to have elastic projections or practically an elastic annular groove into which a flange of a container 1, which is preferably provided in a known manner on the proximal end 5 thereof, is clipped.

However, the holding means 11 has at least two radial projections 13, 13'.

The holding means 11' of the holding device 27 is preferably embodied such that unintended relative movement between a container 1 inserted into the receptacle 29, 29' and the holding device 27—when seen in the axial, radial and in the circumferential direction—is prevented. The container 1 is therefore held in the holding device 27 in such a way that it cannot be moved unintentionally in any of these degrees of freedom. An especially stable support is thus provided. In particular, the container 1 cannot rotate unintentionally relative to the holding device 27 or fall out of it. Likewise, the container 1 does not unintentionally come into contact with the containers 1 arranged in adjacent receptacles. Cosmetic defects are thus avoided.

The holding means 11' is preferably embodied such that it works together with the corresponding holding means 11 of the container 1. This means that the features described in connection with the holding means 11 of the container 1 also apply to the holding means 11' of the holding device 27. Particularly, the holding means 11' is preferably complementary to the holding means 11. It can therefore have commensurate projections, recesses, necks and/or depressions that are preferably complementary to the corresponding elements of the holding means 11. A general description of the holding means 11' will therefore be dispensed with and reference made in this respect to the description of the holding means 11. However, the depicted sample embodiment of the holding device 27 and of the holding means 11' will be discussed specifically.

The holding means 11' comprises at least one projection and/or at least one recess, preferably at least one hook-shaped projection, here specifically two hook-shaped projections 31, 31'. The holding device 27 also has an opening 33 in the area of the recess 29'. A chamber of a container 1 arranged in the 29' is accessible through this. In particular, it is preferably possible to fill the chamber through the opening 33. Very especially preferably, a plug can also be introduced into the container 1 through the opening 33. For example, this can be a middle plug of a dual chamber systems or an end plug of a syringe, carpule or of a dual chamber system. For this, the opening 33 must have a diameter that is at least as large, and preferably slightly larger, than the interior diameter of the container 1 in the area of the chamber to be filled or in the area into which the plug is to be inserted. Preferably, however, the opening 33 is dimensioned with respect to its diameter such that the container 1 can still be supported on the holding device 27 at least with an area of the wall of the base body 3. Accordingly, the diameter of the opening 33 is preferably smaller than an external diameter of the base body 3 in the area with which the base body 3 lies against the holding device 27.

In the depicted sample embodiment, the hook-shaped projections 31, 31' are—when seen in the radial direction of the opening 33—arranged in an opposing manner. Since they are preferably identical, only the projection 31 will be described in further detail in the following.

The projection 31 has an axial neck 35 and a corresponding axial recess 37. As a result of this, the hook shape of the projection 31 is substantially formed. In the locking position of the container 1, the projection 13 engages with the neck 19 into the depression 37, while the neck 35 engages in the depression 21 at the same time. A positive fit is thus created, and the container 1 is held securely on the holding device 27 both in the axial and in the radial direction.

In the depicted sample embodiment, the radial necks 17, 17' are provided on the projection 13 are provided in order to increase the friction between the projection 13 and the projection 31 in order to ensure, in particular, that the container 1 is seated securely—when seen in the circumferential direction—on the holding device 27.

The projection 13' works together in a commensurate manner with the projection 31'.

In the depicted sample embodiment, the container 1 can be swiveled into its locking position. For this purpose, it is first arranged in the receptacle 29 shifted by about 90° to its illustrated position and then swiveled by about 90°, as a result of which the projections 13, 13' and 31, 31' engage with each other, so that the container 1 is finally arranged in its locking position. The projections 13, 13' are supported on a contact surface 39.

Figure 3:
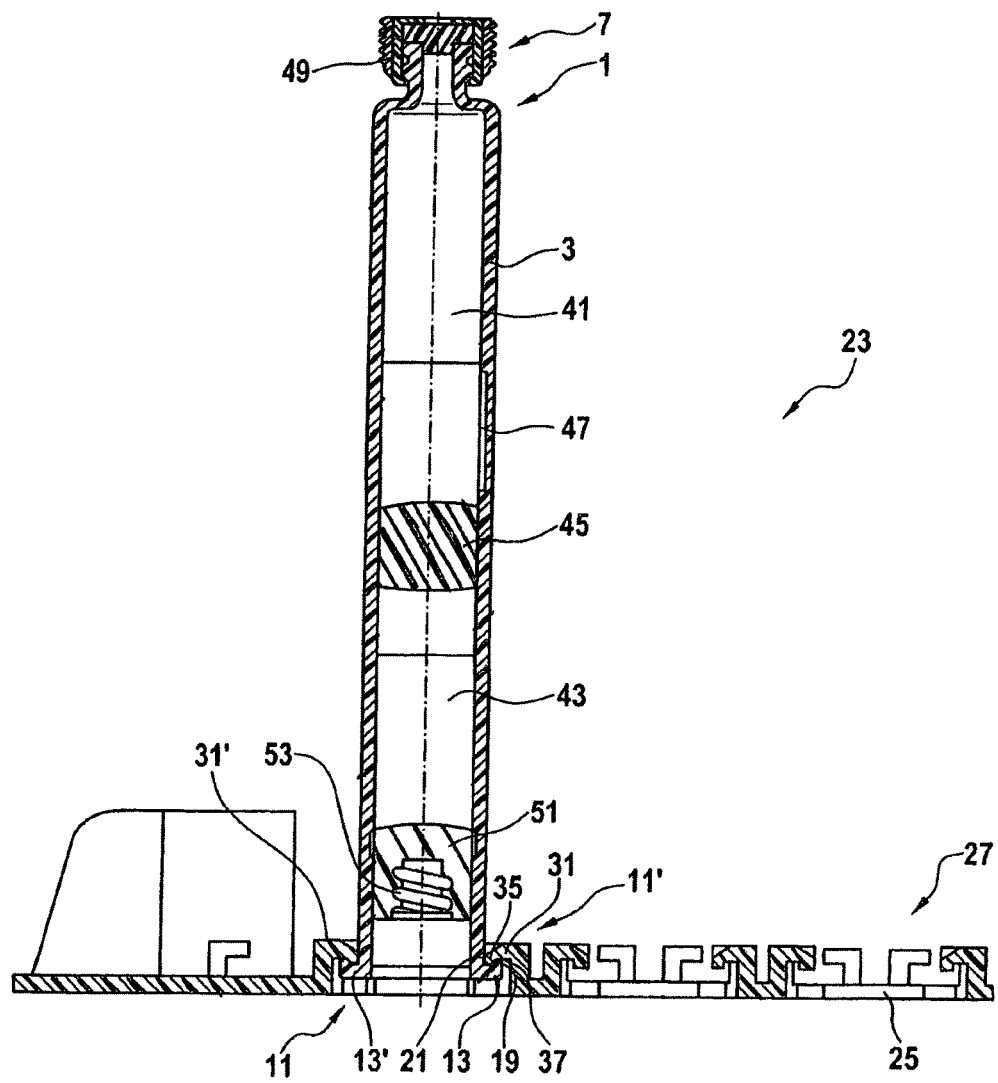
FIG. 3 shows a sectional view of the holding system and of the holding device according to FIG. 2.

FIG. 3 shows a sectional view of the holding system according to FIG. 2. The same and functionally equivalent elements are provided with the same reference symbols, so reference is made to the preceding description in that respect. FIG. 3 also shows that the projection 13 works together with the projection 31 such that the neck 19 engages in the depression 37, whereas the neck 35 engages in the depression 21. The same applies accordingly to the projection 13' and the projection 31'.

The projections 31, 31' face each other along the circumference of the opening 33.

In the sample embodiment shown in FIG. 3, the container 1 is embodied as a dual chamber system. It comprises a distal chamber 41 and a proximal chamber 43 that are separated from each other by a middle plug 45. To activate the dual chamber system, the middle plug 45 can be moved in a known manner into the area of a bypass 47 in order to create a fluid connection between the distal chamber 41 and the proximal chamber 43.

The middle plug 45 can be introduced into the interior of the base body 3 through the opening 33 and hence through the 27 or the carrier system 25.

The distal end 7 of the container 1 is sealed with a closure 49. If the pharmaceutical preparation disposed in the distal chamber 41 is not freeze-dried, it is possible to load the container 1 completely via the opening 33. The container is then sealed for the time being with the closure 49. Then the distal chamber 41 is filled. After that, the middle plug is put in place. Subsequently, the proximal chamber 43 is filled. Finally, an end plug 51 is put in place. This preferably has a connecting means for creating a connection to a piston rod, hear a thread 53.

However, if the pharmaceutical preparation disposed in the distal chamber 41 is to be freeze-dried, a different sequence of filling steps is necessary. Here, the container 1 must be turned. In the depicted sample embodiment, this is possible by turning the holding device 27 or the carrier system 25. Since the container 1 is arranged securely on it, it cannot be unintentionally separated from the carrier system 25 or fall out of it. The appropriate filling of a dual chamber system will be discussed in further detail below.

In the depicted sample embodiments, the container 1 has the at least one holding means 11 at its proximal end 5. In other sample embodiments, it is also possible for the at least one holding means 11 to be arranged in another area of the container 1. For example, a holding means 11 could be arranged on the container 1 more or less in the middle. Accordingly, the holding device 27 would then also be arranged in the corresponding middle area of the container 3. It is also possible to provide at least one holding means 11 at the distal end 7 of the container 1.

As can be seen, in the depicted sample embodiments, the container 1 is substantially locked with the holding device 27 through a rotary or swiveling movement. In doing so, cosmetic defects on the container 1 can occur if it is grasped with a tool that applies the frictional torque necessary for locking. For this reason, the container 1 preferably comprises a connecting element that is embodied such that a tool can be received in a frictionally engaging manner in order to effect a transfer of torque from the tool to the base body. Preferably, an interior wall of the base body 3 in the area of the proximal end 5 can be embodied such that a tool is able to engage frictionally. For example, a square receptacle can be embodied here. Other geometries such as, for example, a hexagonal receptacle, are also conceivable. A multi-sided or similar geometry on the circumferential surface 9 for engaging with a corresponding key is also possible. It is also possible to provide at least one elevation and/or recess on a front-side end of the container 1, which is to say preferably in the area of the proximal end 5 or of the distal end 7, with which a tool can work together to apply the torque required for locking.

Preferably, a plug connection can also be provided in which the container 1 is introduced in the longitudinal direction into a commensurately embodied receptacle of the holding device 27.

Preferably, at least one of the holding means 11, 11' has a descending surface. In the depicted sample embodiment, it is possible, for example, for the base of the depression 37 or the base of the depression 21 to be embodied as a descending surface. Said surface then preferable descends when seen in the circumferential direction. Accordingly, the depression having the descending surface—when seen in the circumferential direction—has a variable depth. Preferably, the deepest area of the depression is the first to engage with the neck engaging in it. Upon further motion in the direction toward the locking position, the depth of the depression decreases until the corresponding neck lies against the base thereof. Preferably, at least one of the two holding means 11, 11' to be joined together has a certain elasticity, so that further movement in the direction toward the locking position is possible, upon which at least one of the two elements is deformed at least slightly. This results in a pretensioning force that acts against an unintentional separation of the connection. The at least one descending surface can drop off at an appropriate angle so that self-locking occurs in this area.

A commensurately descending surface can also be provided on the neck 35 or the neck 19. It is also possible to provide descending surfaces on holding means that are different from those shown in the sample embodiments.

It is possible to provide preferably at least one elastically movable locking element, for example an elastically supported rod or a catch or snap-in pin, that preferably initially springs or swivels back as a result of a descending surface upon engagement of the corresponding holding means in order to finally lock in the locking position into an undercut which—when seen in the direction of insertion—is arranged behind the descending surface acting as a lead-in chamfer. Depending on the type of connection, the direction of insertion can coincide with the longitudinal direction (plug connection) or with a circumferential direction of the container 1 (rotary or swivel connection).

Figure 3A:
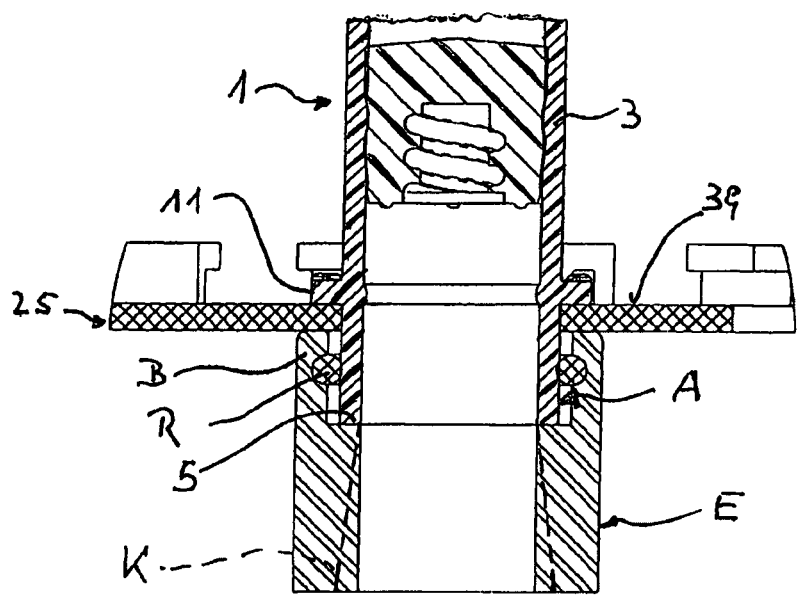
FIG. 3A shows a sectional view of the holding system with a modified sample embodiment of the container.

FIG. 3A shows an enlarged sectional view of the holding system according to FIG. 3. The same and functionally equivalent elements are provided with the same reference symbols, so reference is made to the preceding description in that respect.

FIG. 3A shows a modified sample embodiment of the container 1 in whose proximal end 5 is inserted an end plug 51. The container 1 differs from those shown in FIG. 2 in that the holding means 11 is not provided directly on the proximal end 5 of the container, but rather at a distance thereto. If the holding means 11 of the container 1 is coupled with a holding means 11' of a receptacle 29 of a holding device 27, then a proximal section A of the base body 3 of the container 1 protrudes from the carrier system 25. FIG. 3A shows that the base body 3 protrudes up over the carrier system 25 and lies with its holding means 11 against the contact surface 39 of the carrier system 25. On the opposing side of the contact surface 39, the section A protrudes out of the carrier system 25. Preferably, the section A is embodied in a single piece with the base body 3 of the container 1, as is shown in FIG. 3A.

It follows from FIG. 3A that an insertion aid E can preferably be placed onto the section A whose internal diameter corresponds to the internal diameter of the base body 3 of the container 1. The insertion aid E is provided with an attachment flange that engages around the section A from the outside so that the insertion aid E is held securely on the section A.

In the sample embodiment shown here, a connecting element is provided, here preferably as an O-ring R, between the exterior surface of the section A and the interior surface of the attachment flange B.

In the sample embodiment shown in FIG. 3A, the insertion aid E is cylindrical. Likewise, the attachment B is cylindrical, which is to say annular. It is quite conceivable, however, for this attachment flange B not to be embodied as a closed ring but rather to have a number of individual attachment arms by means of which the insertion aid E is held on the section A of the base body 3.

The annular design of the attachment flange B is preferred especially in conjunction with the O-ring R. In this way, it is possible, namely, to place the insertion aid E tightly onto the proximal section A of the base body 3 of the container 1. A plugging device can then be placed on the insertion aid E such that a vacuum builds up on the interior of the container before a plug is then inserted. The O-ring therefore seals the insertion aid E off with respect to the section A so that the vacuum can build up in the container 1 without loss.

During plugging, the insertion aid E can also serve as an orientation aid for the plugging device. An optimal orientation of this device with respect to the container 1 to be provided with a plug is therefore possible.

After all of this, it is evident from FIG. 3A that, in the modified sample embodiment of the container 1, its holding means 11, like in the sample embodiment of the container 1 that was first described, lie against the contact surface 39 of the carrier system 25. However, in the sample embodiment according to FIG. 3A, the base body 3 of the container 1 protrudes through the carrier system 25, so that a section A of the base body 3 protrudes beyond the side of the carrier system 25 opposite the contact surface 39. It is therefore possible to place an insertion aid E onto the section A which facilitates the introduction of one or more plugs into the interior of the container 1. The so-called plugging, and hence the filling process of the container 1 as well, is improved substantially as a result.

It is especially advantageous here if the inner surface of the insertion E transitions into the inner surface of the section A so that a plug introduced into the insertion aid E can be transferred very easily into the base body 3 of the container 1

It is also evident that the section A protruding beyond the carrier system 25 already simplifies plugging even if no insertion aid E of the kind described in FIG. 3A is provided. A plugging device can therefore be arranged directly on the section A. Nonetheless, plugging can be especially simplified and the filling process thus improved by means of this insertion aid E.

It is readily evident from the remarks on FIG. 3A that the insertion aid E, which is cylindrical here and has a cylindrical interior space, can also be provided with a conical interior space having a larger internal diameter at the end of the insertion aid E facing away from the section A than at the end associated with the section A. The free end of the insertion aid E therefore has a larger interior diameter than the base body 3 and the section A. A plug can therefore be introduced very easily into the free end of the insertion aid E and then transferred into the interior of the base body 3, particularly if equal internal diameters are provided in the transitional area from the interior space of the insertion aid E to the interior space of the section A, thus resulting in the provision of a smooth transition from the insertion aid E to the section A.

In FIG. 3A, a conical interior space of the insertion aid E is indicated by a dashed line K. The angle of inclination of this line K with respect to a cylindrical inner surface can be adapted to different plugs that are used in conjunction with the container 1. The more the plugs have to be compressed upon insertion into the container 1, the greater the angle of inclination of the conical interior area is preferably selected. In other words, the greater the angle of inclination of the line K with respect to the—here cylindrical—inner surface of the insertion aid E, the further the interior space of the insertion aid opens up in the direction of its free end.

From the remarks above, it is readily clear that the conical internal area in the insertion aid E need not extend over the entire length of the insertion aid E from its free end to the end of the section A. It is sufficient if a conical area is embodied directly at the free end of the insertion aid E in order to facilitate the insertion of a plug.

What is more, it is possible to embody the edge of the interior space in the area of the free end of the insertion aid E with a radius in order to facilitate the insertion of a plug.

Figure 4:
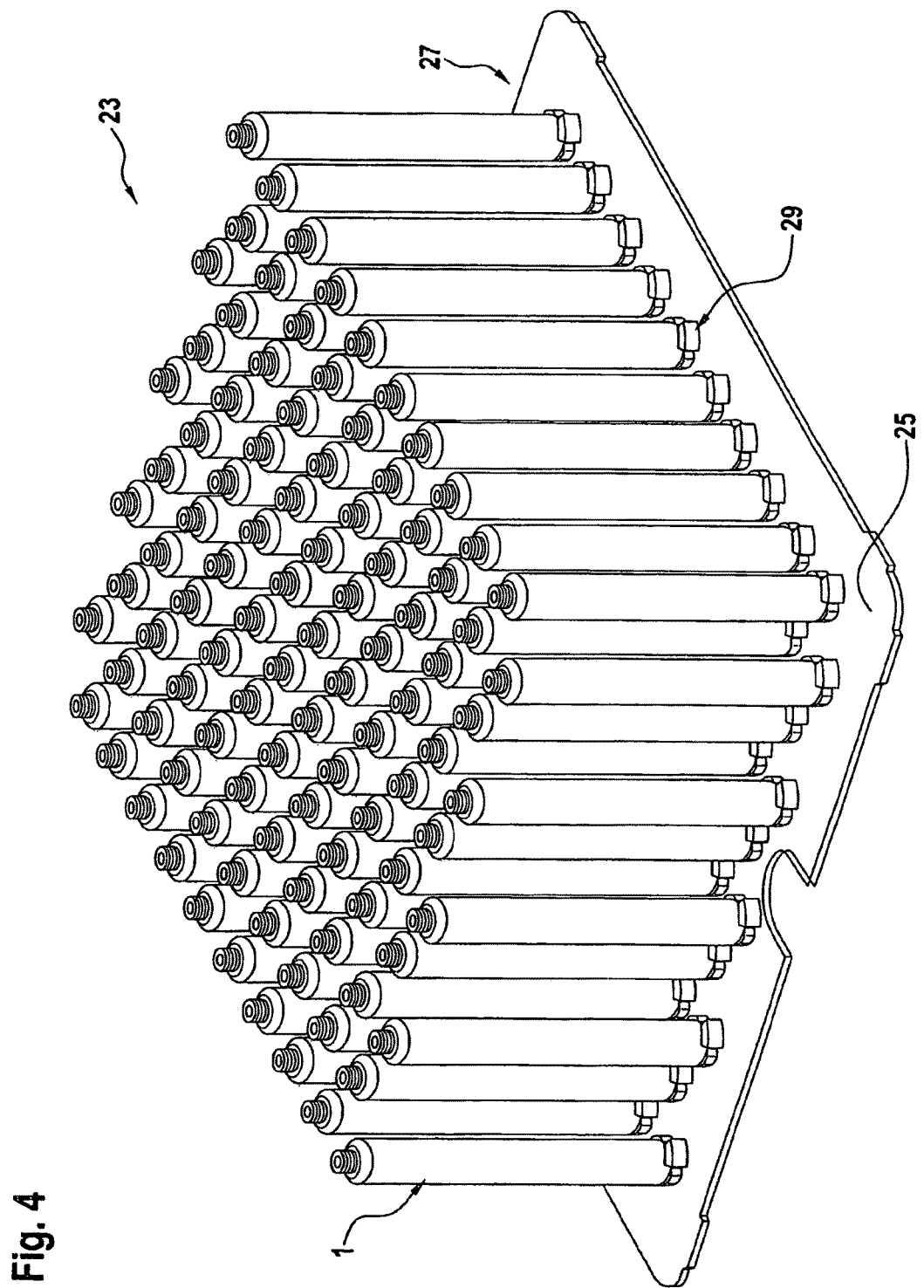
FIG. 4 shows the holding system according to FIG. 2 with several containers arranged in receptacles of the carrier system embodied as a holding device.

FIG. 4 shows the holding system according to FIG. 2 with a representation of the complete carrier system 25. The same and functionally equivalent elements are provided with the same reference symbols, so reference is made to the preceding description in that respect. In the depicted sample embodiment, a container 1 is arranged in each of the receptacles, of which only the receptacle 29 is provided with a reference symbol here for the sake of example. It becomes clear that the depicted sample embodiment of the carrier system 25 is a nest in a nest/tub configuration in which a predetermined number of pre-sterilized containers 1 can be delivered and handled. It is also evident that, in order to fill the containers 1, only the carrier system 25 need be grasped. Consequently, it is not necessary to grasp the individual containers 1 and arrange them in separate devices. Since the containers 1 are held securely and firmly on the carrier system 25, the entire filling process can be carried out in a very simple and even automated manner given that the containers are simultaneously grasped or handled via the carrier system.

Figure 5:
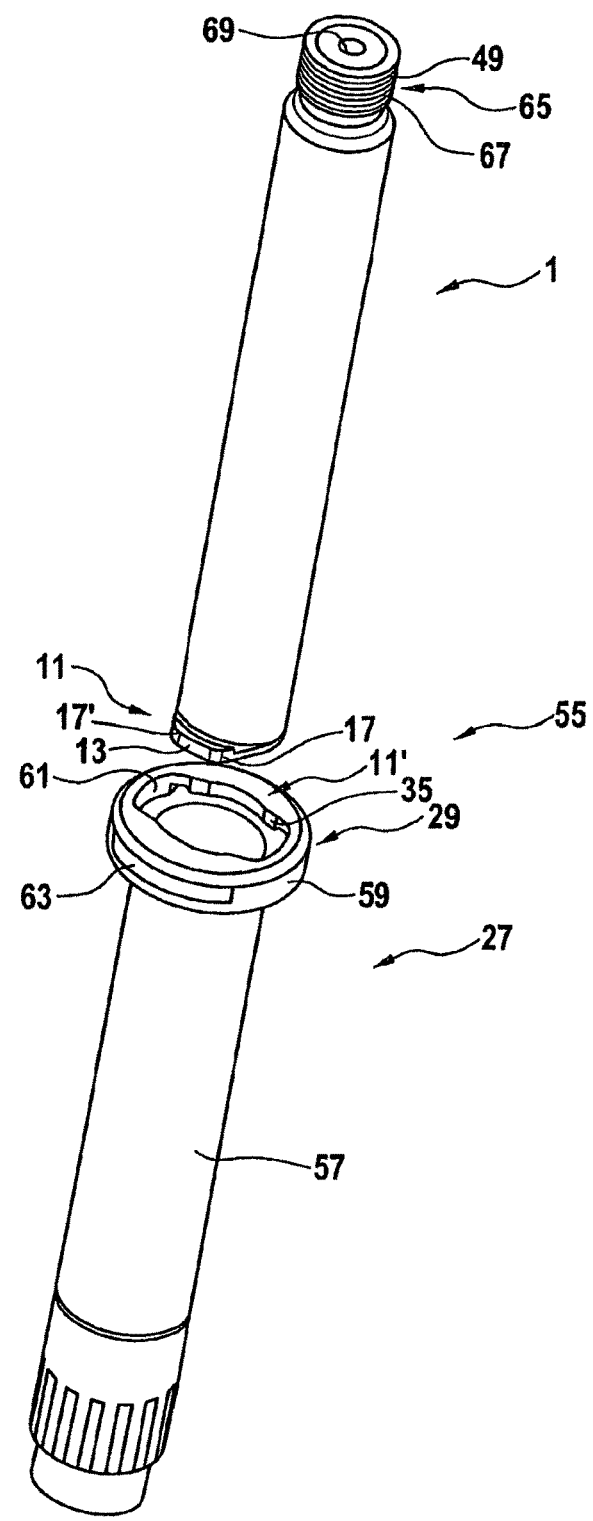
FIG. 5 shows an exploded view of sample embodiment of an injection aid with a holding device embodied as a mechanical part for the injection aid as well as a container.

FIG. 5 shows an injection aid 55 in a partially disassembled state. The holding device 27 is embodied here as a mechanical part 57 for the injection aid 55. The same and functionally equivalent elements are provided with the same reference symbols, so reference is made to the preceding description in that respect. The mechanical part 57, which is embodied as a holding device 27, has a receptacle 29. This comprises a holding means 11' which is embodied here substantially identical to the holding means 11' of the holding device 27 of FIGS. 1 to 4. However, in the depicted sample embodiment, instead of the two projections 31, 31', a retaining ring 59 is provided on which the neck 35 and the depression 37 (not shown here) as well as the opposing elements (also not shown here), namely the corresponding neck and the corresponding depression, are arranged. The ring 59 also has a front-side opening 61 through which the container 1 can be inserted with its holding means 11 into the receptacle 29. The opening 61 has a shape that is complementary to the holding means 11, so that the container 1 can only be inserted in a position that is pivoted about 90° around the longitudinal axis relative to the depicted locking position.

Moreover, the holding means 11, 11' can be connected in the same manner as is the case with respect to the sample embodiments already described. Deviations from the depicted configuration with respect to other sample embodiments that were already described but not shown, for example in terms of a plug connection, are also readily possible. Projections 31, 31' can also be provided instead of the ring 59.

In the depicted sample embodiment, the retaining ring 59 also has two radial slits of which here only the slot 63 is shown. The projection 13 engages into this. Accordingly, the projection 13' engages into the opposing slot, which is not shown. It is also possible not to provide slots in this area but wall sections, in which case increased friction then preferably occurs with the wall sections in the area of the necks 17, 17'. As will readily be understood, it is also possible for the wall sections to have corresponding depressions into which the necks 17, 17' engage preferably in a locking manner.

Especially preferably, at least one of the holding means 11, 11' has a certain elasticity, and the dimensions of the holding means 11, 11' are selected such that, in the connected or locked state, a pretensioning force acts on the connection that holds the container 1 especially securely, firmly and stably on the holding device 27. It becomes clear that a front housing part to the receptacle of the container 1 can be omitted. The injection aid 55 therefore has an especially simple construction.

In known injection aids that have a front housing part to the receptacle of the container 1, a connecting element is typically provided on a distal end thereof in order to connect an injection element, for example a cannula, to the injection aid 55.

In the depicted sample embodiment, a connecting element 65 is preferably provided on the closure 49 of the container 1. It is embodied here as a thread 67. This can cog with a corresponding thread provided on an injection element. The closure 49 also has a sealing element which is embodied here as a septum 69.

Figure 6:
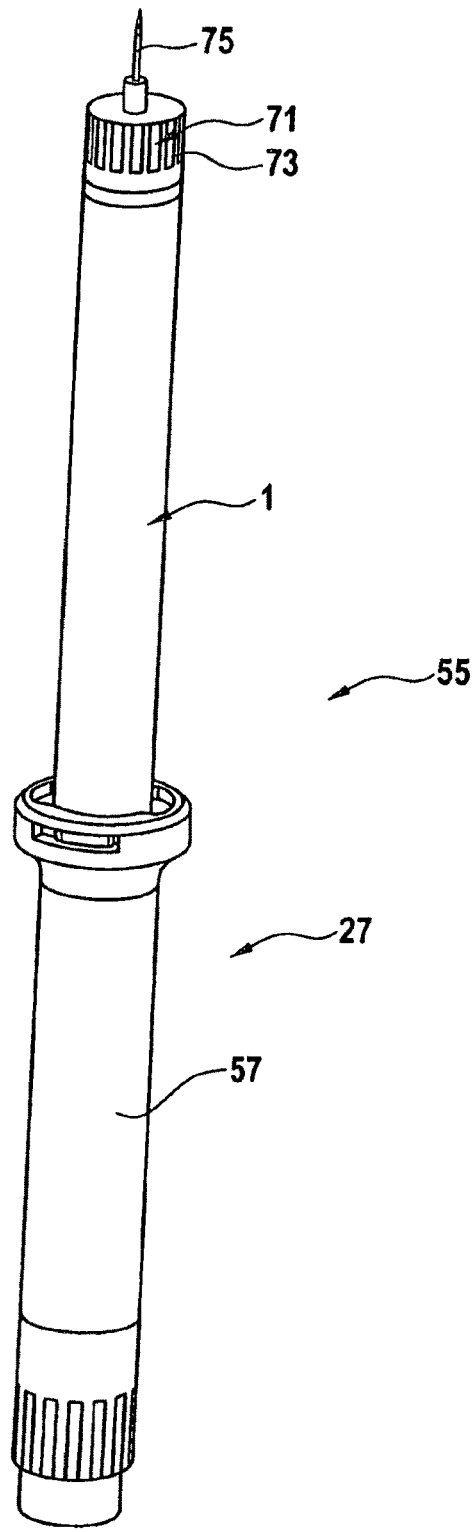
FIG. 6 shows the injection aid according to FIG. 5 in the assembled state.

FIG. 6 shows the injection aid 55 according to FIG. 5 in the assembled state. The same and functionally equivalent elements are provided with the same reference symbols, so reference is made to the preceding description in that respect. Arranged in the area of the closure 49 (not shown here) is an injection element 71. This has an internal thread (not shown) that cog with the external thread 67 (also not shown) of the closure 49. The injection element 71 comprises a holding element 73 with the corresponding internal thread as well as an injection needle 75 held by the holding element 73 or arranged on same.

Figure 7:
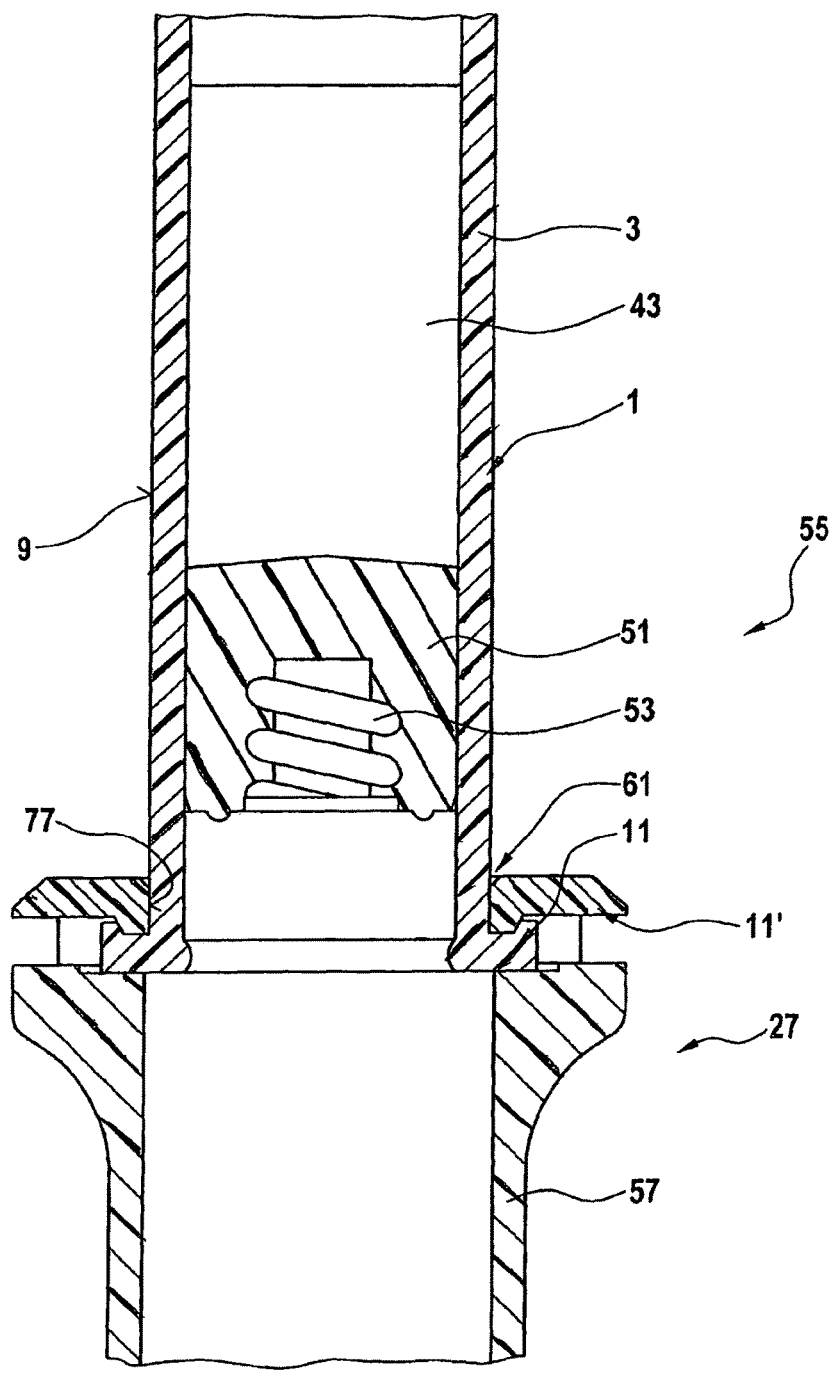
FIG. 7 shows a sectional detailed view of the injection aid according to FIG. 5.

FIG. 7 shows a detailed sectional view of the injection aid 55 according to FIG. 5. The same and functionally equivalent elements are provided with the same reference symbols, so reference is made to the preceding description in that respect. The mechanical part 57 comprises the elements necessary for the preparation and execution of an injection with the injection aid 55. If the container 1 is embodied as a dual chamber system, the mechanical part 57 also comprises the elements necessary for a reconstitution of the preparation disposed in the distal chamber. Particularly, the mechanical part 57 comprises a piston rod (not shown here) that engages with the end plug 51 preferably with the aid of the thread 53.

In order to ensure trouble-free preparation and execution of the injection, the container 1 and the mechanical part 57 must be centered relative to each other. This means that the longitudinal axes of the container 1 and of the mechanical part 57 must coincide.

The centering is preferably achieved via the opening 61. As shown in FIG. 5, the opening 61 preferably does not have a constant internal diameter, but rather one which varies along the circumference thereof. Nevertheless, it preferably has an area in which the internal diameter corresponds approximately to the external diameter of the base body 3. The container 1 is centered relative to the mechanical part 57 as a result of the circumferential surface 9 of the base body 3 lying against an inner surface of the opening 61. Especially preferably, the interior diameter of the opening 61 is smaller in areas than the external diameter of the base body 3. Either the base body 3 or the holding element 11' is preferably elastic in the area of the opening 61, so that a frictional connection, loaded with a pretensioning force, results in the area of contact of the circumferential surface 9 with the inner surface 77. Preferably, the holding element 11' is elastic in this area. Overall, especially secure centering is achieved in this way.

In another sample embodiment, the centering is achieved via the piston rod (not shown here) of the mechanical part 57. The piston rod then preferably has an external diameter that corresponds to the internal diameter of the base body 3 at least in the area of insertion of the piston rod, so that the base body 3 is centered relative to the mechanical part 57 when the piston rod is inserted into same.

Figure 8:
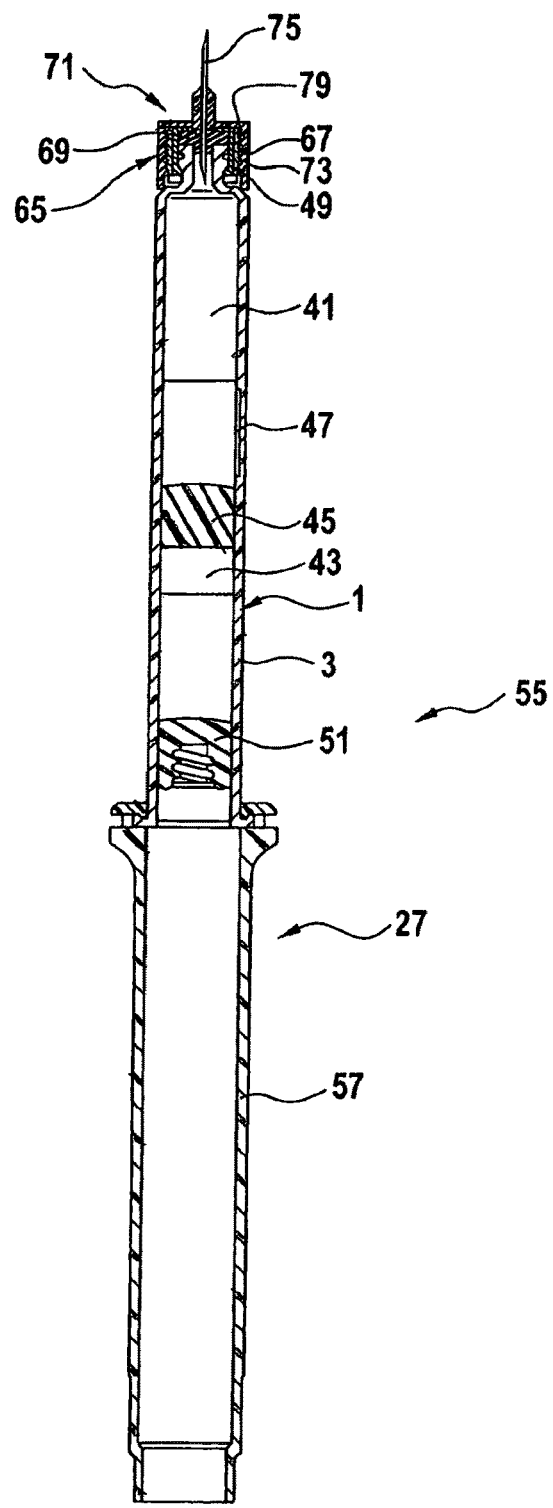
FIG. 8 shows a sectional view of the injection aid according to FIG. 6.

FIG. 8 shows a complete longitudinal sectional view of the injection aid 55 according to FIG. 6. The same and functionally equivalent elements are provided with the same reference symbols, so reference is made to the preceding description in that respect. Shown here is particularly the injection element 71. This is arranged on the closure 49 with the aid of the connecting element 65. An internal thread 79 of the holding element 73 cogs with the external thread 67 of the closure 49.

The injection element 71 comprises the injection needle 75 which, in the depicted sample embodiment, is ground into a point not only on its distal end but on its proximal end as well. It protrudes through the septum 69 with its distal end when the injection element 71 is arranged on the closure 49. As a result, a fluid path is formed from the distal chamber 41 via the injection needle 75 into the vicinity of the base body 3, so that a pharmaceutical substance disposed in the distal chamber 41 can finally be injected.

It turns out that a holding means 11 provided on the container 1 can also work together with sample embodiments other than those described thus far. For example, system components for additional process steps, for example the labeling of the container 1, can have an appropriate holding device in order to grasp or hold the container 1.

System components for the handling, activation and/or application of the container 1 or of the pharmaceutical preparation disposed in the container 1 can also be embodied as an appropriate holding device or comprise such a holding device.

Figure 9:
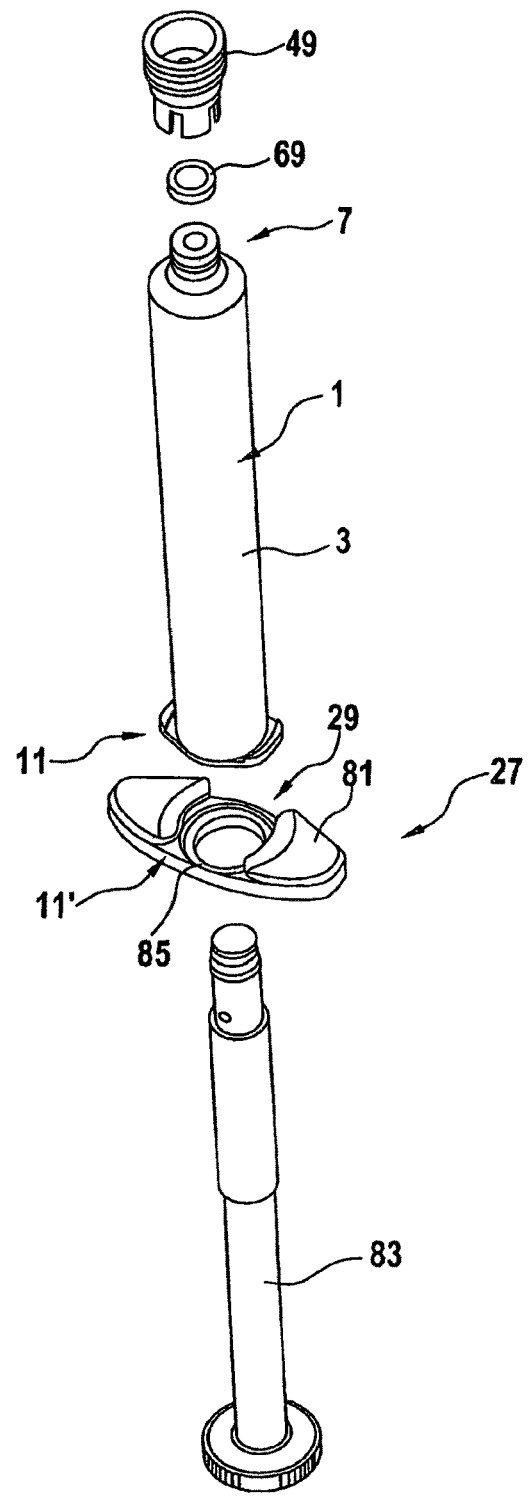
FIG. 9 shows an exploded view of a container, a holding device embodied as a finger rest, a piston rod and a closure.

FIG. 9 shows another sample embodiment of a holding device 27 which is embodied here as a finger rest 81. The same and functionally equivalent elements are provided with the same reference symbols, so reference is made to the preceding description in that respect. Also shown in FIG. 9 in the exploded view is the container with the closure 49, the sealing element or septum 69 and a piston rod 83. The finger rest 81 has a receptacle 29 with a holding means 11' which can work together with the holding means 11 of the container 1 such that the base body 3 of the container 1 is held securely on the holding device 27 or the finger rest 81. The holding means 11, 11' is preferably embodied in one of the previously described manners.

Here, the finger rest comprises—when seen in a radial direction—an inwardly projecting ring 85. Its interior diameter is preferably smaller than the interior diameter of the proximal opening of the base body 3. As a result, the ring 85 acts as a retaining element, for example as a so-called backstop, which prevents the retraction of the end plug 51 from the base body 3.

Such a retaining element for the end plug 51 can also be provided in another, inherently known manner on the finger rest 81. It is possible for the retaining element not to hold back the end plug 51 directly but to work together with the piston rod 83 in a manner that does not permit the end plug 51 to shift back beyond a certain position.

The closure 49 is embodied here in a known manner as a closure that is appropriate for freeze-drying which can be arranged on the container 1 in a first locking position in which a fluid path into the vicinity of the container 1 is cleared in order to enable freeze-drying. It can also be arranged in a second locking position in which it securely seals its distal end 7.

Figure 10:
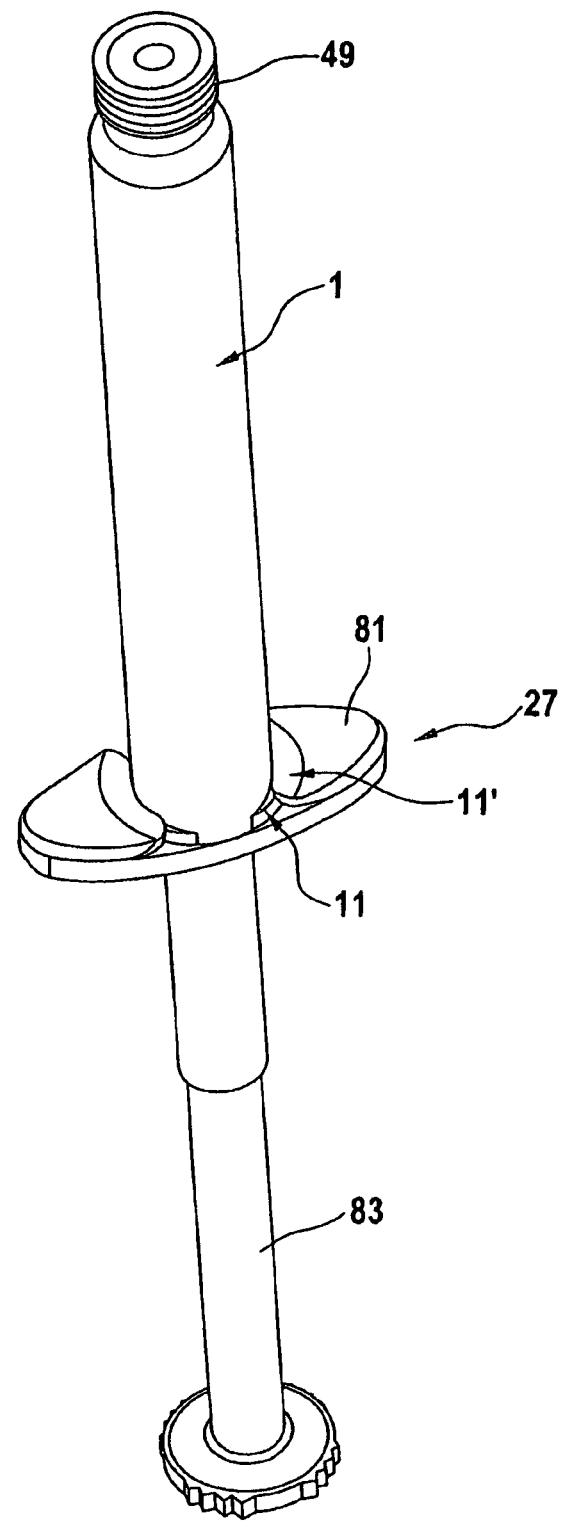
FIG. 10 shows the elements according to FIG. 9 in the assembled state.

FIG. 10 shows the sample embodiment according to FIG. 9 in the assembled state. The same and functionally equivalent elements are provided with the same reference symbol, so reference is made to the previous description in this respect. The finger rest 81 is connected here to the container 1 via the holding means 11, 11'. The holding means 11, 11' are preferably locked together.

The following can also be seen: A locking connection of the holding means 11, 11' can optionally be provided such that the connection cannot be broken again in a nondestructive manner. This is particularly the case if elastic locking elements first retract or swing back, for example as a result of lead-in chamfers and then engage in an undercut. If the holding elements 11, 11' are non-detachably locked together, the holding device 27 is discarded with the container 1. In contrast, if the holding elements 11, 11' are detachably connected to each other, the holding device 27 can optionally be reused even if the container 1 is discarded after use.

Figure 11:
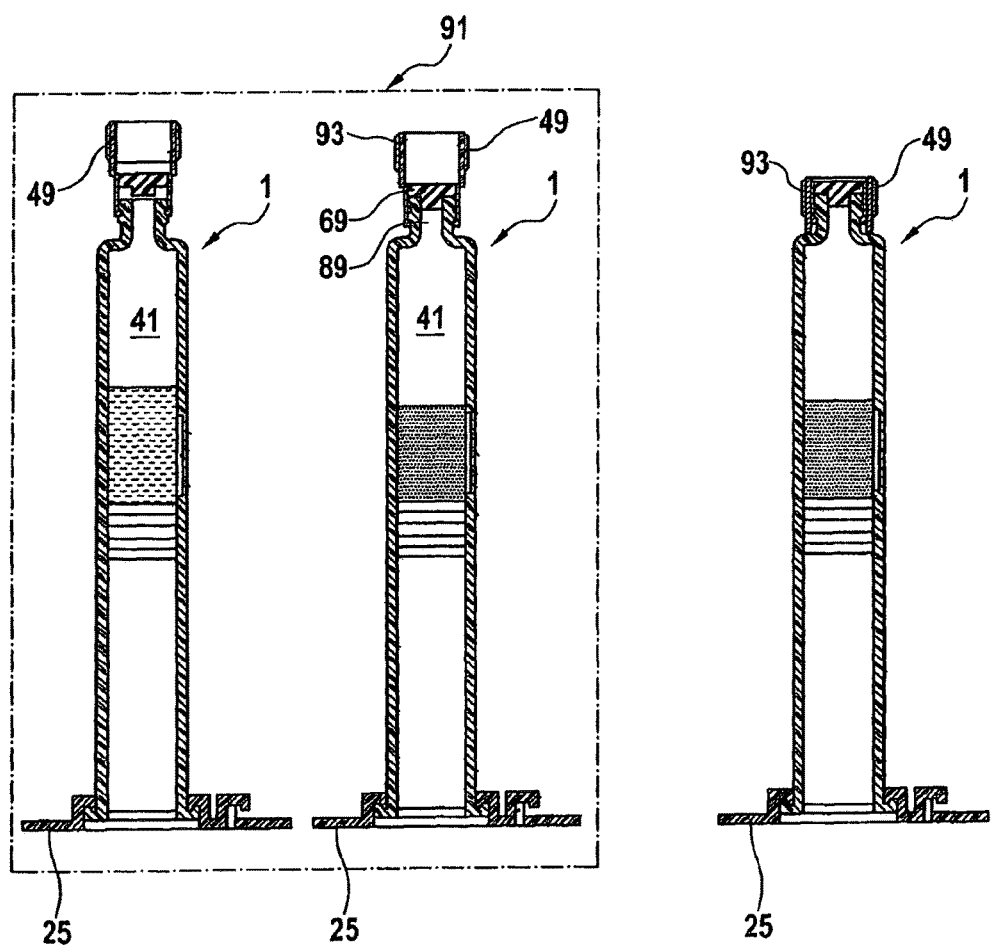
FIG. 11 shows a schematic representation of the filling of a container embodied as a dual chamber system using a holding system comprising a carrier system embodied as a holding device.
Figure 11:
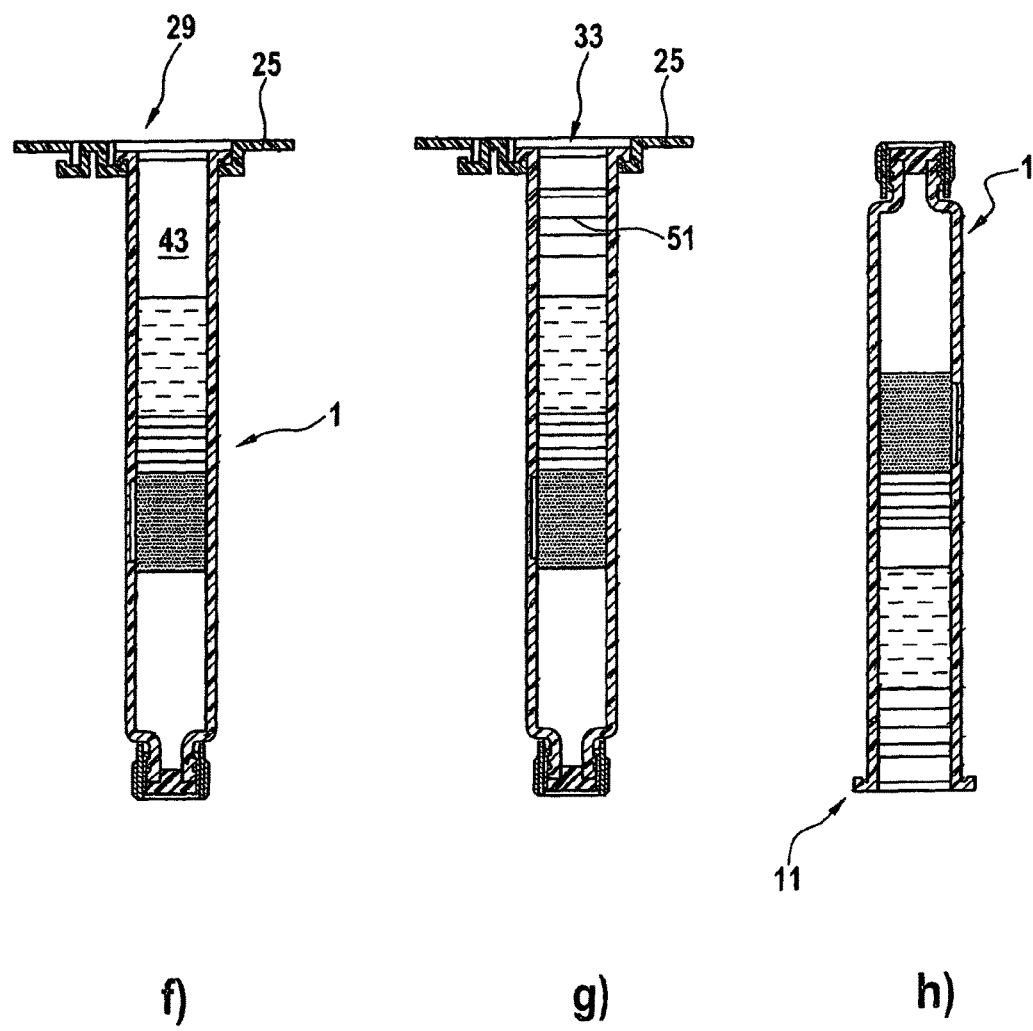

FIG. 11 shows a schematic representation of a method for filling a container 1 which is embodied as a dual chamber system, with a pharmaceutical preparation being freeze-dried in the distal chamber 41. The same and functionally equivalent elements are provided with the same reference symbols, so reference is made to the preceding description in that respect.

Shown at the far left in FIG. 11 is a holding system 23 which comprises a tub element 87 in which the carrier system 25 is arranged. This comprises receptacles 29 in which containers 1 are arranged. The holding system 23 preferably corresponds to the tub/nest configuration, with the tub element 87 being embodied as a tub and the carrier system 25 or the holding device 27 being embodied as a nest. Preferably, the tub element 87 is sealed with a film element (not shown). After the holding system 23 has been brought into a clean room, the film element is removed and the tub element 87 thus opened. It is then possible, through the carrier system 25, to arrange the middle plug 45 in the container 1. Preferably, this is performed in a parallel manner for all of the containers 1 disposed in the carrier system 25—as well as the other process steps. However, the process steps are explained here for the sake of example with reference to one container 1. However, the placement of the middle plug 45 can also be done after the carrier system 25 has already been removed from the tub element 87.

Next, the carrier system 25 is turned, resulting in the configuration shown in FIG. 11a). The distal chamber 41 is preferably filled through a distal opening 89 of the container 1.

As shown in FIG. 11b), the closure 49 is then arranged in an inherently known manner in a first locking position on the container 1, with a fluid path from the distal chamber 41 into the vicinity of the container 1 remaining.

Subsequently, the carrier system 25 is brought with the containers 1 into a freeze-dryer 91, which is shown here schematically.

FIG. 11 c) shows the container 1 before freeze-drying. FIG. 11d) shows the container 1 after freeze-drying, and after the closure 49 has been arranged in its second locking position in which the septum 69 or the corresponding sealing element tightly seals the opening 89. Only one retaining ring 93 must still be put into its retaining position in which it holds the closure 49 securely onto the container 1.

During the entire process, and particularly during freeze-drying as well, the containers 1 remain arranged on the carrier system 25. This is comparatively thin and light and preferably comprises plastic. This saves energy, particularly during cooling and subsequent warming during and after freeze-drying, because the heat capacity of the carrier systems 25 is low. In comparison to this, conventional containers must be sorted into massive metal or steel hoppers which have a high heat capacity and are also more difficult to handle. A carrier system 25 comprising plastic or comprised of plastic can be discarded following the method portrayed here. In contrast, the known metal or steel hoppers must be subjected to elaborate cleaning and sterilization or autoclaving. In this respect as well, the carrier system 25 therefore makes for a simpler process control. The tub element 87 preferably also comprises or is comprised of plastic.

In FIG. 11e), the carrier system 25 is discharged from the freeze-dryer 91 with the containers 1. The retaining ring 93 is now arranged in its retaining position, so that the closure 49 is arranged securely and firmly on the container 1.

In order to fill the proximal chamber 43 as shown in FIG. 11f), the containers 1 must be turned. This is done here by simply turning the carrier system 25. Since the containers 1 are arranged securely in the receptacles 29, they cannot fall out and it is readily possible to turn the containers 1 together with the aid of the carrier system 25.

Finally, in the step shown in FIG. 11g), the end plug 51 is placed through the carrier system 25 or the opening 33.

FIG. 11h) shows the container 1, which is now no longer engaging with the carrier system 25. It is preferably subjected to another final control before it is sent for continued use. As already described, the holding means 11 can be used here in order to bring the container 1 into engagement with other holding devices or a labeling system or with an injection aid.

Overall, it is evident that the proposed container 1, the proposed holding device 27, the proposed holding system 23, and the proposed injection aid 55 are characterized by an especially secure and stable connection that is achieved with the aid of holding means 11, 11'. As a result, the handling even of several containers 1 is simplified substantially. What is more, cosmetic defects on the containers 1 can be reliably prevented. The injection aid 55 can be manufactured in a simple manner without great logistical effort and therefore at low cost.

The invention claimed is:

1. An arrangement for pharmaceutical preparations comprising:
   a carrier device including a generally planar contact surface and a plurality of fill openings extending through the contact surface, each fill opening associated with a holding device;
   a container having a base body elongated along an axis, a sidewall and a proximal open end; and
   at least one first holding element extending from the container, the at least one first holding element cooperating with the holding device for the container to hold a proximal-most surface of the container against the generally planar contact surface such that the proximal open end is aligned with one of the fill openings,
   the at least one first holding element includes at least one first flange extending perpendicular to the axis and at least one projection extending from the first flange, disposed parallel to the axis, and spaced from the sidewall to define a recess therebetween;
   wherein the at least one first holding element including the at least one first flange and at least one projection perpendicular to the first flange is part of the container and removable from the carrier device along with the container.

2. The arrangement as set forth in claim 1, wherein the at least one first holding element and/or the recess includes on a circumferential surface thereof at least one radial neck and/or at least one radial depression.

3. The arrangement as set forth in claim 1, wherein the at least one projection and/or the recess includes at least one axial neck and/or at least one axial depression in the form of a groove.

4. The arrangement as set forth in claim 1, wherein the at least one projection and/or the recess includes at least one descending surface, with the at least one descending surface provided as a lead-in chamfer for attachment of the at least one first holding element to a corresponding second holding element of the holding device.

5. The arrangement as set forth in claim 1 in combination with the holding device, the at least one first holding element cooperating with a corresponding second holding element of the holding device to define a bayonet joint.

6. The arrangement as set forth in claim 1, further comprising a connecting element, for frictional receiving of a tool, so that torque can be transferred from the tool to the base body to create a connection between the at least one first holding element and a corresponding second holding element of the holding device.

7. The arrangement as set forth in claim 1, wherein the container is selected from a group consisting of a syringe, carpule, vial and a dual chamber system.

8. The arrangement as set forth in claim 1, wherein the at least one first holding element includes a plurality of first holding elements, each fill opening of the carrier device associated with an associated one of the plurality of holding elements.

9. The arrangement for pharmaceutical preparations of claim 1, wherein the at least one holding element and a corresponding holding device cooperate to define a bayonet joint, the bayonet joint including a plug-and-turn mechanism in which the holding element is turned about an axis during insertion into the corresponding holding device in the direction of the axis.

10. The arrangement for pharmaceutical preparations of claim 1, wherein the carrier device includes an upper facing surface defining the contact surface and an opposite lower facing surface, the open proximal end of the container being open to the lower facing surface through one of the fill openings.

11. An arrangement for pharmaceutical preparations, the arrangement comprising:
    a holding device including a generally planar contact surface and at least one fill opening extending through the generally planar contact surface in a direction perpendicular to the plane defined by the generally planar contact surface, each fill opening associated with a first radially extending holding device flange carrying a first axially extending holding device projection, the generally planar contact surface extending beyond the first radially extending holding device flange of each fill opening; and
    at least one container, each container including a generally cylindrical base body having an open proximal end and a first radially extending container flange carrying a first axially extending container projection, the first axially extending container projection radially spaced from the base body to define a first recess therebetween;
    wherein the first axially extending holding device projection is received in the first recess for securely holding a proximal-most surface of the container against the generally planar contact surface of the holding device such that the proximal open end is immediately adjacent to and aligns with the at least one fill opening.

12. The arrangement as set forth in claim 11, wherein each container further includes a second radially extending container flange carrying a second axially extending container projection, and each fill opening is associated with a second radially extending holding device flange carrying a second axially extending holding device projection, the second axially extending holding device projection received in a second recess radially between the second axially extending container projection and the base body.

13. The arrangement as set forth in claim 12, wherein each of the first radially extending container flange, first radially extending holding device flange, second radially extending container flange, and second radially extending holding device flange are perpendicular to an axis of the base body.

14. The arrangement for pharmaceutical preparations of claim 11, wherein the at least one container includes a plurality of containers.

15. The arrangement for pharmaceutical preparations of claim 14, wherein the containers of the plurality of containers are oriented parallel to one another.

16. The arrangement as set forth in claim 11, wherein the holding device includes an upper facing surface defining the contact surface and an opposite lower facing surface, the open proximal end of the container being open to the lower facing surface through one of the fill openings.

17. An arrangement for transporting and filling a plurality of pharmaceutical containers, the arrangement comprising:
    a carrier device including a generally planar contact surface, a plurality of fill openings extending through the generally planar contact surface in a direction perpendicular to the plane defined by the generally planar contact surface such that the generally planar contact surface extends between each fill opening, and a holding device associated with each of the fill openings, each holding device including a first radially extending holding device flange carrying a first axially extending holding device projection; and a plurality of pharmaceutical containers, each pharmaceutical container including a generally cylindrical base body having an open proximal end and a container flange carrying a first axially extending container projection, the first axially extending container projection radially spaced from the base body to define a first recess therebetween, each pharmaceutical container secured to the generally planar contact surface of the carrier device by one of the holding devices such that a proximal-most surface of each pharmaceutical container is held against the generally planar contact surface, and the proximal open end of each pharmaceutical container is immediately adjacent to and aligns with an associated fill opening and the first axially extending holding device projection is received in the first recess.

18. The arrangement for transporting and filling a plurality of pharmaceutical containers of claim 17, wherein the pharmaceutical containers are oriented parallel to one another.

19. The arrangement for transporting and filling a plurality of pharmaceutical containers of claim 17, wherein the plurality of pharmaceutical containers are syringes.

20. The arrangement for transporting and filling a plurality of pharmaceutical containers of claim 17, wherein the carrier device includes an upper facing surface defining the contact surface and an opposite lower facing surface, the open proximal end of the container being open to the lower facing surface through one of the fill openings.

* * * * *